(12) United States Patent
Saggers

(10) Patent No.: US 10,369,042 B2
(45) Date of Patent: Aug. 6, 2019

(54) THERMAL PACKS FOR THERAPEUTIC TREATMENT

(75) Inventor: Mike Saggers, Bedfordshire (GB)

(73) Assignee: GIOCO LIMITED, Barton-le-Clay, Bedfordshire (GB)

( * ) Notice: Subject to any disclaimer, the term of this patent is extended or adjusted under 35 U.S.C. 154(b) by 841 days.

(21) Appl. No.: 13/988,145

(22) PCT Filed: Nov. 17, 2011

(86) PCT No.: PCT/GB2011/052249
§ 371 (c)(1),
(2), (4) Date: Jul. 23, 2013

(87) PCT Pub. No.: WO2012/066339
PCT Pub. Date: May 24, 2012

(65) Prior Publication Data
US 2013/0296981 A1 Nov. 7, 2013

(30) Foreign Application Priority Data

Nov. 17, 2010 (GB) .................................. 1019446.2
Nov. 17, 2010 (GB) .................................. 1019453.8

(51) Int. Cl.
*A61F 7/00* (2006.01)
*A61F 7/02* (2006.01)

(52) U.S. Cl.
CPC .............. *A61F 7/0085* (2013.01); *A61F 7/02* (2013.01); *A61F 2007/0054* (2013.01); *A61F 2007/0095* (2013.01)

(58) Field of Classification Search
CPC .............................................. A61F 2007/0056
See application file for complete search history.

(56) References Cited

U.S. PATENT DOCUMENTS

| 4,108,146 | A | | 8/1978 | Golden | |
|---|---|---|---|---|---|
| 4,821,354 | A | * | 4/1989 | Little | A47C 1/143 138/103 |
| 5,330,519 | A | | 7/1994 | Mason | |
| 5,383,919 | A | | 1/1995 | Kelly et al. | |
| 5,806,335 | A | * | 9/1998 | Herbert | A61F 7/10 607/114 |

(Continued)

OTHER PUBLICATIONS

International Search Report and Written Opinion, in corresponding International application No. PCT/GB2011/052249, International filing date Nov. 17, 2011.

(Continued)

*Primary Examiner* — Kaitlyn E Smith
(74) *Attorney, Agent, or Firm* — Donald E. Stout; Stout, Uxa & Buyan, LLP

(57) ABSTRACT

A thermal pack (10) and associated control system (32, 44) for the therapeutic treatment of a mammal. The pack (10) is made from a flexible, heat conductive, liquid impermeable material and has an inlet (18) through which fluid can be transferred into the pack (10), a passageway through which fluid can flow and an outlet (20) through which fluid may be removed from the pack (10). The passageway within the pack (10) also has a separator element (22) that forms a track (22, 24) along which the fluid can flow and keeps the walls of the pack (1) spaced apart so that the fluid flow is not restricted if the pack (10) is flexed in use.

19 Claims, 6 Drawing Sheets

(56) References Cited

U.S. PATENT DOCUMENTS

| | | | |
|---|---|---|---|
| 6,086,609 A * | 7/2000 | Buckley | A61F 7/10 607/104 |
| 6,197,045 B1 | 3/2001 | Carson | |
| 6,238,427 B1 | 5/2001 | Matta | |
| 7,204,041 B1 | 4/2007 | Bailey, Sr. | |
| 7,640,764 B2 * | 1/2010 | Gammons | A61F 7/0085 607/104 |
| 8,613,762 B2 * | 12/2013 | Bledsoe | A61F 7/02 165/46 |
| 2003/0019476 A1 | 1/2003 | Chambers | |
| 2004/0068309 A1 * | 4/2004 | Edelman | A61F 7/02 607/104 |
| 2004/0068310 A1 * | 4/2004 | Edelman | A61F 7/02 607/104 |
| 2004/0158303 A1 * | 8/2004 | Lennox | A61F 7/0085 607/109 |
| 2005/0096714 A1 * | 5/2005 | Freedman, Jr. | A61F 7/00 607/104 |
| 2008/0060374 A1 * | 3/2008 | Gammons | A61F 7/0085 62/259.3 |
| 2009/0254160 A1 * | 10/2009 | Shawver | A61F 7/02 607/104 |
| 2012/0158103 A1 * | 6/2012 | Bledsoe | A61F 7/02 607/104 |
| 2012/0172957 A1 | 7/2012 | Dewaegenaere | |
| 2012/0310312 A1 * | 12/2012 | Yee | A61F 7/12 607/105 |
| 2013/0013033 A1 * | 1/2013 | Lowe | A61N 1/39 607/104 |
| 2014/0222121 A1 * | 8/2014 | Spence | A41D 13/005 607/104 |
| 2014/0243939 A1 * | 8/2014 | Lowe | A61F 7/02 607/104 |
| 2014/0277302 A1 * | 9/2014 | Weber | A61F 7/0085 607/104 |
| 2015/0190274 A1 * | 7/2015 | Landy | A61F 7/12 607/106 |
| 2016/0128865 A1 * | 5/2016 | Lowe | A61N 1/39 607/104 |
| 2016/0166428 A1 * | 6/2016 | Hilton | A61F 7/02 607/104 |

OTHER PUBLICATIONS

Related U.S. Appl. No. 14/118,860.

* cited by examiner

THERMAL PACKS FOR THERAPEUTIC TREATMENT

This application claims priority to PCT International Application No. PCT/GB2011/052249, having an international filing date of Nov. 17, 2011, and entitled Improvements in Thermal Packs for Therapeutic Treatment, which in turn claims priority to Great Britain Application No. 1019453.8, filed on Nov. 17, 2010, and to Great Britain Application No. 1019446.2, filed on Nov. 17, 2010. All of the foregoing applications are herein expressly incorporated by reference, in their entirety.

This invention relates to a therapeutic device for external application to a mammal and a control system for use with the therapeutic device. More particularly the therapeutic device is used for the heating, or cooling of a selected area of a mammalian body, especially of the human body.

The therapeutic device takes the form of a heat conductive bladder that will conform to the various contours of the body to aid in the therapeutic treatment of sports injuries and other forms of trauma, to relieve post operative pain, and to control swelling, bruising and engorgement.

Devices for applying heat or cold, such as a heat pack or cold pack, to areas of the human body are well known. Known ice packs, for example, may comprise sealed enclosures which contain particulate matter, water, glycol, a mixture thereof or other fluid medium which are pre-chilled in a refrigerating device and the chilled or, in some cases, frozen pack then applied to an area of the skin of a human or other mammalian body to treat and/or control inflammation, bruising and/or infection and to promote healing and/or to relieve pain.

However, such cold pack devices have disadvantageous aspects and are of limited use since they tend to be too intense in their cooling effect when first applied and have been found to induce frostbite. Moreover, the ice packs lose much of their effectiveness because they warm up rather quickly through heat exchange with the body, thereby providing a constantly changing temperature at the areas of contact. Other devices in which the heat exchange with the body, and hence the therapeutic treatment, is prolonged are known. These other known devices with prolonged effectiveness include flexible sealed enclosures through which a chilled or heated fluid medium is caused to flow by pumping the fluid medium through the device. Such devices are known in the art by various descriptions such as garments, bladders, bandages, pads, wraps, cuffs and the like, but in each case the device generally comprises a flexible sealed enclosure (hereinafter a 'thermal pack') which can be applied and secured to an area of the body to be treated. A chilled or heated fluid medium can be caused to flow through the enclosure to provide a cooling or heated therapeutic treatment.

In relation specifically to cold therapy treatment, or cryotherapy as it is known, equipment to circulate fluid through a thermal pack generally comprises a chiller unit supplying cold fluid to a thermal pack by way of circulation through insulated hoses. More simplistic (and cheaper) systems operate by raising and lowering a water-ice tank to fill and then empty a thermal pack via a single hose. These systems should not be confused with the cold packs referred to above such as gel filled flexible enclosures which are placed in a freezer and then applied to the treatment area of the body without any circulation or ingress or egress of fluid relative to the pack.

An effective therapy requires the maintenance of a constant even temperature at a desirable level over the treatment area. The various cooling techniques presently in use fail satisfactorily to maintain a constant temperature on the desired body areas or do so only with the use of expensive and unnecessarily complex equipment. In addition to the requirement of maintaining a constant temperature on the selected areas, there is also a need for a thermal pack that will comfortably and securely fit the contours of the area being treated as well as a need for providing portability of the cooling (or heating) unit. Application of the thermal pack to an area of the body, e.g. the knee, causes it to fold and crease creating restrictions which reduce or cut off the flow of fluid and causes "dead areas" with little or no fluid movement which results in loss of temperature control at that point. Accordingly, there is a need for ensuring uninterrupted flow and dispersion of fluid over the complete surface of the thermal pack.

A first aspect of the present invention provides a thermal pack for therapeutic treatment of a mammal which pack comprises a flexible, heat conductive liquid impermeable bladder which has means for the ingress and egress of a fluid medium, the bladder comprising a pair of superposed sheets secured together so as to provide a fluid passageway within the bladder and a separator element within the fluid passageway to mitigate restrictions in the fluid flow through the passageway when the pack is flexed, in use, out of the plane of the superposed sheets, for example wherein the separator element is formed from material which is less flexible relative to the superposed sheets and/or comprises a structure or framework, for example that prevents the fluid passageway from collapsing when the pack is so flexed.

According to another feature of this aspect of the invention the means for the ingress and egress of fluid may comprise an inlet for the ingress of fluid into the fluid passageway and/or an outlet for the egress of fluid from the fluid passageway and/or wherein the fluid passageway extends through the pack from the inlet to the outlet. Preferably, the separator device extends through the fluid passageway between the inlet and the outlet.

According to a further feature of this aspect of the invention the separator device may provide or comprise a fluid conveying track which may extend throughout the fluid passageway, e.g. between the superposed sheets and/or maintain the superposed sheets in spaced apart relationship, for example at least in the vicinity of the track. Preferably, the fluid conveying track comprises two or more, for example a plurality of side by side channels.

According to a still further feature of this aspect of the invention the separator element may comprise a multiplicity of discrete spacers that may be disposed at various locations within the fluid passageway, for example so as to maintain the superposed sheets in substantially spaced apart relationship.

According to another feature of this aspect of the invention the or each separator device may be secured in position within the fluid passageway, e.g. at one or more locations to one or both of the superposed sheets.

According to yet another feature of this aspect of the invention the superposed sheets may be formed from polyurethane and/or the separator device is formed from a moulded or mouldable plastics material, for example an injection moulded plastics material.

A second aspect of the present invention provides a fluid control system, for example for use with a thermal pack as described above, such as to provide a therapeutic treatment system. The fluid control system may be configured to supply fluid to a heat exchanger, e.g. to the thermal pack, at a substantially constant temperature and/or to maintain the temperature of fluid in the thermal pack or any other heat exchanger device at a substantially constant temperature. The system may comprise a first volume of fluid and/or a second volume of fluid with a temperature differential therebetween. Means may be provided for the mutual exchange of fluids between the first and second volumes of fluids, for example in response to the temperature of fluid supplied by the system to the thermal pack or heat exchanger, for example in order to maintain the flow of fluid through the thermal pack or heat exchanger at a substantially constant temperature.

Preferably, the system comprises a first fluid containing tank and a second fluid containing tank. The system may maintain a temperature differential between the first and second tanks. One of the tanks may be adapted to supply fluid to the thermal pack or heat exchanger device, e.g. so that the temperature of the fluid flowing through the thermal pack or heat exchanger device may be maintained at a substantially constant temperature. Means may be provided to create a fluid flow from the said one tank through the thermal pack or heat exchanger device. Means may also be provided to create a fluid flow between the first and second tanks and/or control means may be provided to activate and/or control the operation of the fluid flow creation means, for example to provide a mutual exchange of fluid between the first and second fluid containing tanks, e.g. in order to stabilise the temperature of the fluid supplied to the thermal pack or heat exchanger device.

Preferably, the means or the first fluid containing tank comprises a fluid pump, for example to supply fluid from that tank to the second fluid containing tank. The means or the second fluid containing tank may comprise a fluid pump, for example to supply fluid from the second tank to a conduit or other means adapted to provide a fluid connection with the thermal pack or heat exchange device. Temperature monitoring means such as a temperature sensor may be provided, e.g. to monitor the temperature of fluid flow through the thermal pack or heat exchanger device and/or return fluid passageway means may be provided, for example to allow a mutual exchange of fluids between the first and second fluid containing tanks. Control means such as a controller may be provided, for example to cause said mutual exchange of fluids, e.g. in response to information provided to the controller or control means, for example by the temperature monitoring means or sensor. The fluid control system or control means or controller may be configured to cause or ensure a constant flow between the first and second fluid containing tanks, for example only varying the flow rate proportionally with respect to the information provided by the temperature monitoring means or sensor, in use.

It is also preferable that the first and second fluid containing tanks are provided in a single unit, e.g. with a separating wall between the tanks. The fluid pump from the first tank may convey fluid to the second tank through the separating wall and/or the return fluid passageway may be provided in the separating wall for the overflow return of fluid from the second tank to the first tank, for example in response to commands from the control means. The fluid pump of the first tank may be submerged or submersed, e.g. in use, in the fluid of the first tank. The fluid of the second tank may be submerged or submersed, e.g. in use, in the fluid of the second tank.

The fluid control system may be provided in a single, e.g. integral, unit or unitary structure.

According to a further feature of the second aspect of the invention the heat exchanger comprises a thermal pack, e.g. as described above, for example for therapeutic treatment by which heated or chilled fluid may be supplied by the system to the thermal pack and/or maintained at a substantially constant temperature for the duration of the therapeutic treatment.

Another aspect of the invention provides the combination of a fluid control system, for example as described above and a thermal pack, for example as described above.

Embodiments of the invention will now be described, by way of example, with reference to the accompanying drawings, in which.

Figure 1:
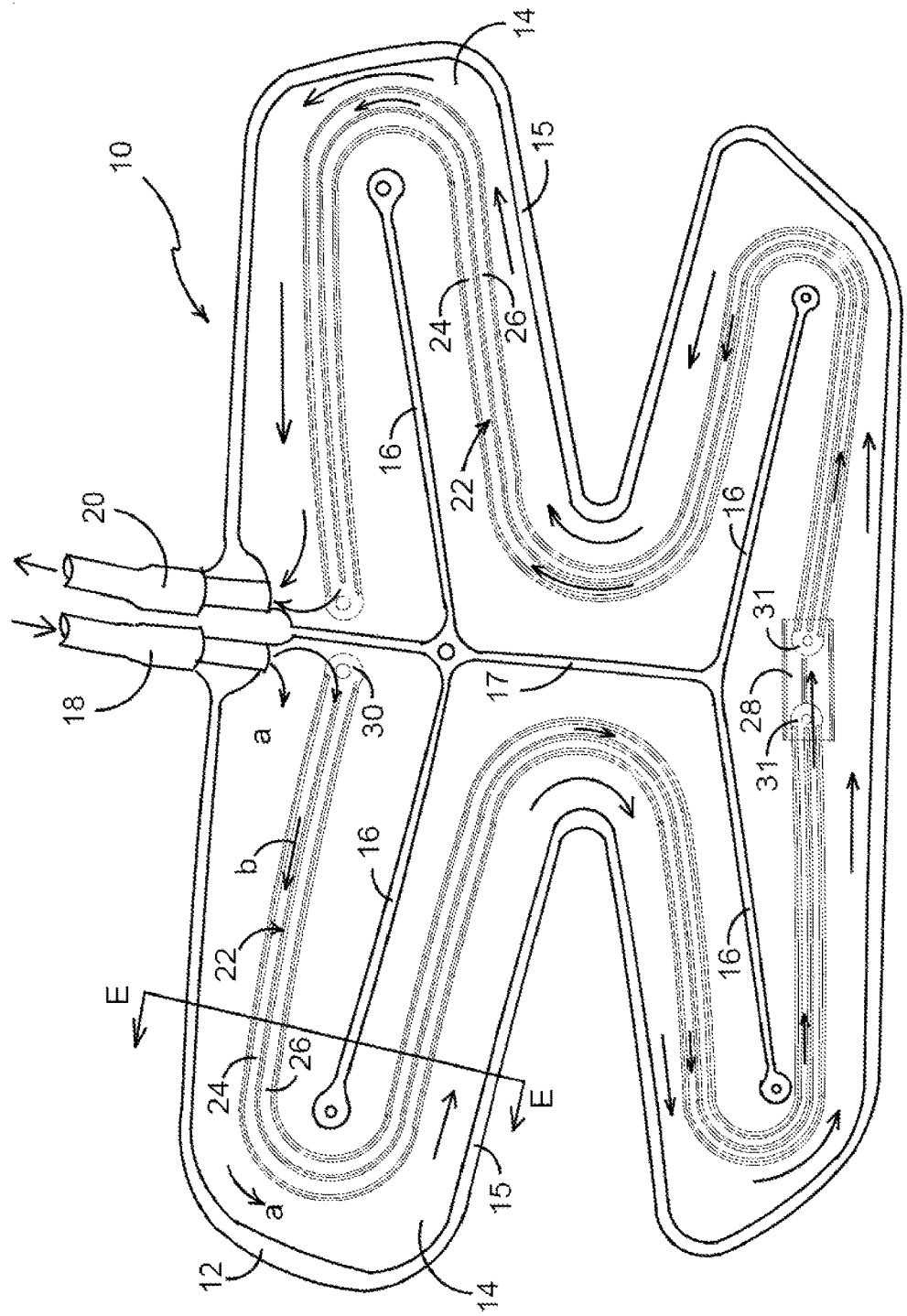
FIG. 1 is a plan view of a first thermal pack according to the invention, shown in flat unfolded condition.

Referring first to FIG. 1 of the drawings, there is shown a thermal pack 10 which comprises a sealed bladder of heat conducting and water impermeable material. The pack 10 includes a back sheet 12 and a front sheet 14, which are secured in superposed relationship and preferably are welded together around their peripheries 15 and also preferably in selected areas 16 in the body of the pack which includes a central spine 17. The front sheet and the back sheet are formed from polyurethane. In this particular embodiment the thermal pack is generally in form of an "H" comprising a double set of wings and which is symmetrical about the central spine and is shaped to be particularly useful for the therapeutic treatment of a knee, elbow or ankle.

The therapeutic pack 10 is able to contain and convey fluid supplied to the unwelded areas of the interior of the pack. An inlet nozzle 18 welded between the sheets of the pack supplies fluid to the wings of the pack so that fluid can circulate between the front sheet and the back sheet of the pack and be discharged from an exit nozzle 20 which is welded in position alongside the inlet nozzle 18. The unwelded areas of the superposed sheets provide a continuous fluid passageway through the thermal pack, and the fluid low is shown by arrows 'a'.

In order to ensure uninterrupted flow of fluid through the pack, one or more separator elements 22 (shown more clearly in FIG. 3) are provided within the fluid passageway of the pack and therefore disposed between the front sheet and the back sheet. In this particular embodiment of the invention, the separator element comprises a pair of "W" shaped tracks which are disposed between the front and back sheets on either side of the central spine 17 of the pack. The tracks each comprise a pair of side by side channels 24, 26 which may be integral and which are formed from relatively stiff (mouldable plastics) material as compared to the front and back sheets and permit the flow of fluid through the channels around the pack. The two "W" shaped components of the separator element are connected together by a bridging piece 28 so that fluid which enters the pack through the inlet nozzle 18 can flow between the back sheet and the front sheet and also along the channels of the separating element as shown by arrows 'b' and then exit through the outlet nozzle 20. Thus, the separator element in the form of a fluid conveying track, not only maintains a spaced apart relationship between the front sheet and the back sheet 12, 14 at least in the vicinity of the track but also provides a fluid 'highway' running through the pack. However, the separator element 22 may be configured to cooperate with the one or both of the sheets 12, 14 to provide such tracks.

The separator element is connected to the top skin of the pack by a number of studs 30 provided adjacent the inlet and outlet nozzles with further studs 31 on either side of the bridging piece 28. Otherwise the separator element is unattached to either one of the sheets of the pack. It will be understood that the studs 31 or indeed any other connector or connection means, may be secured to either or both sheets 12, 14.

The separator element may take numerous forms, for example that which is described below in relation to FIGS. 3 & 4. Some designs will not necessarily permit the element itself to convey fluid between the front and back sheets of the thermal pack. However, in each case, the separator device should function so as to maintain fluid flow through the pack between the front and back sheets when it is in use. In use, the thermal pack almost always is flexed out of the plane of the superposed sheets to bring it into a folded and compressed condition around the contours of an area of the body such as, for example, a knee, elbow, ankle or shoulder. Some separator element designs may also be configured to provide a tortuous flow path, for example to maximise heat transfer between the fluid and the sheets 12, 14 in use.

Figure 2:
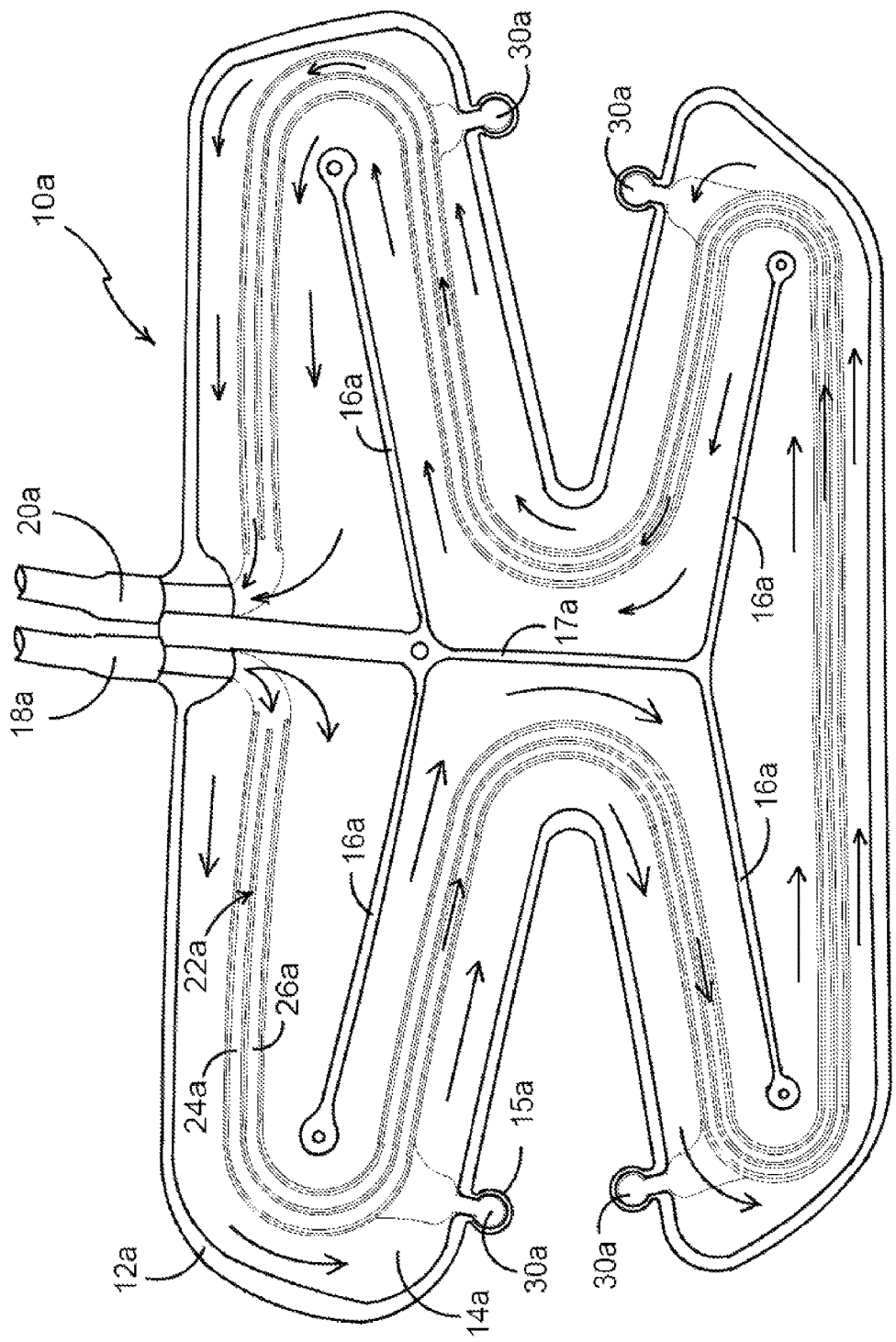
FIG. 2 is a plan view of another thermal pack according to the invention, shown in flat unfolded condition.

FIG. 2 of the drawings shows a second embodiment of a thermal pack according to the invention in which like parts of the embodiment of FIG. 1 are designated like reference numerals, with the addition of the suffix "a". In this second embodiment, the separator element comprises a continuous and tortuous fluid conveying track which extends between the inlet nozzle and the outlet nozzle between the front and back sheets of the pack. As is the case in the first embodiment, the track can convey the fluid medium, which also flows around the pack, between the unwelded faces of the front and back sheets. However, in this embodiment, the track does not include a bridging piece, but is continuous throughout the pack and is held in position by welded studs 30a external to the main outer perimeter of the pack.

Figure 3:
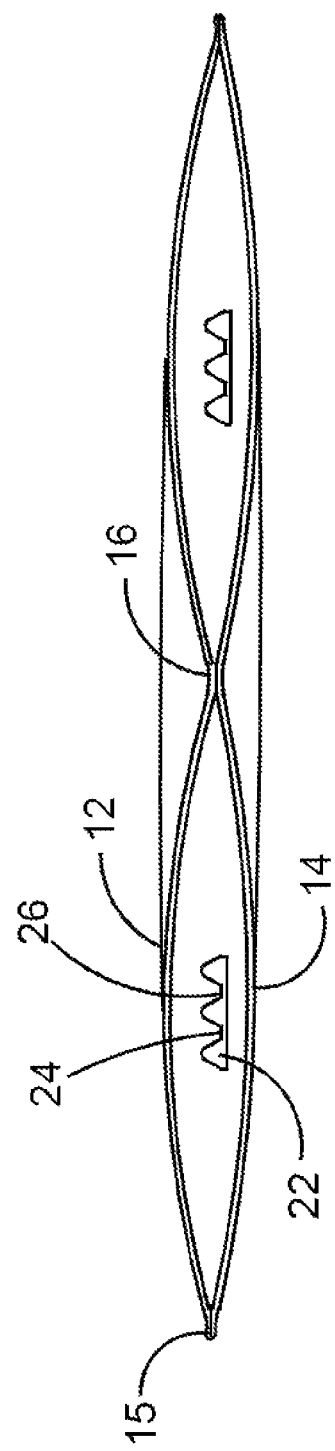
FIG. 3 is a cross-sectional view taken on the line 'EE' of FIG. 1.
Figure 4A:
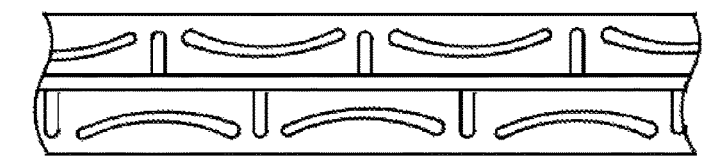
FIG. 4 shows a variety of separator elements which may be incorporated in a thermal pack according to the invention.
Figure 4B:
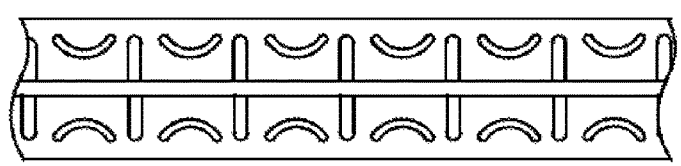
Figure 4C:
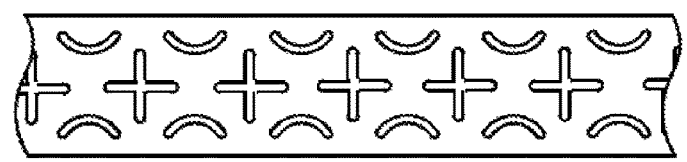
Figure 4D:
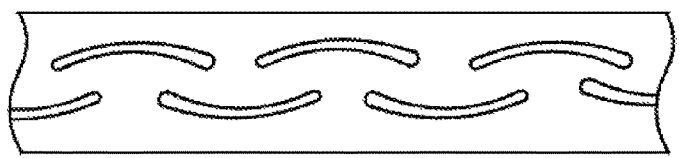
Figure 4E:
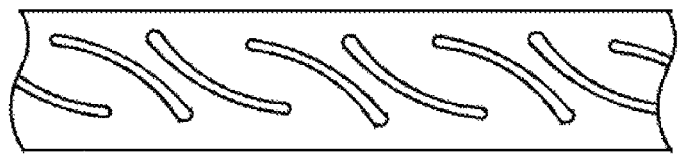

FIG. 3 of the drawings shows a cross-sectional view taken on the line 'EE' of FIG. 1 in which like parts of the embodiment of FIG. 1 are designated like reference numerals. In this view the "W" shaped components of the separator element 22 can be seen within the pack. As described above, the pack includes a back sheet 12 and a front sheet 14, which are secured in superposed relationship and are welded together around their peripheries 15 and in selected areas 16 in the body of the pack. The separator elements 22 are provided within the fluid passageway of the pack and disposed between the front sheet 14 and the back sheet 12 and within the passageway. The separator element 22 comprises a pair of "W" shaped tracks which are each comprise a pair of side by side channels 24, 26 which are formed from relatively stiff materials as compared to the front and back sheets 14, 12. The "W" shaped tracks provide a fluid 'highway' that permits the flow of fluid around the pack. The "W" shaped components of the separator element 22 also maintain the spaced apart relationship of the front sheet 14 and back sheet 12 at least in the vicinity of the track.

Whilst the separator element may comprise a multiplicity of separating elements of various sizes, shapes and dispositions between the sheets, a number of examples are illustrated in FIG. 4 of the drawings, specifically in examples 4a, 4b, 4c, 4d and 4e. In some cases the separator device may comprise a plurality of discrete "islands" between the front and back sheets of the pack which are sufficient in number to maintain substantially uninterrupted flow of the fluid medium through the thermal pack no matter what its configuration, but not so numerous as to inhibit the effective therapeutic treatment by virtue of the presence of the separator "islands" causing reduction in heat transfer between the thermal pack and the treatment area.

Figure 5:
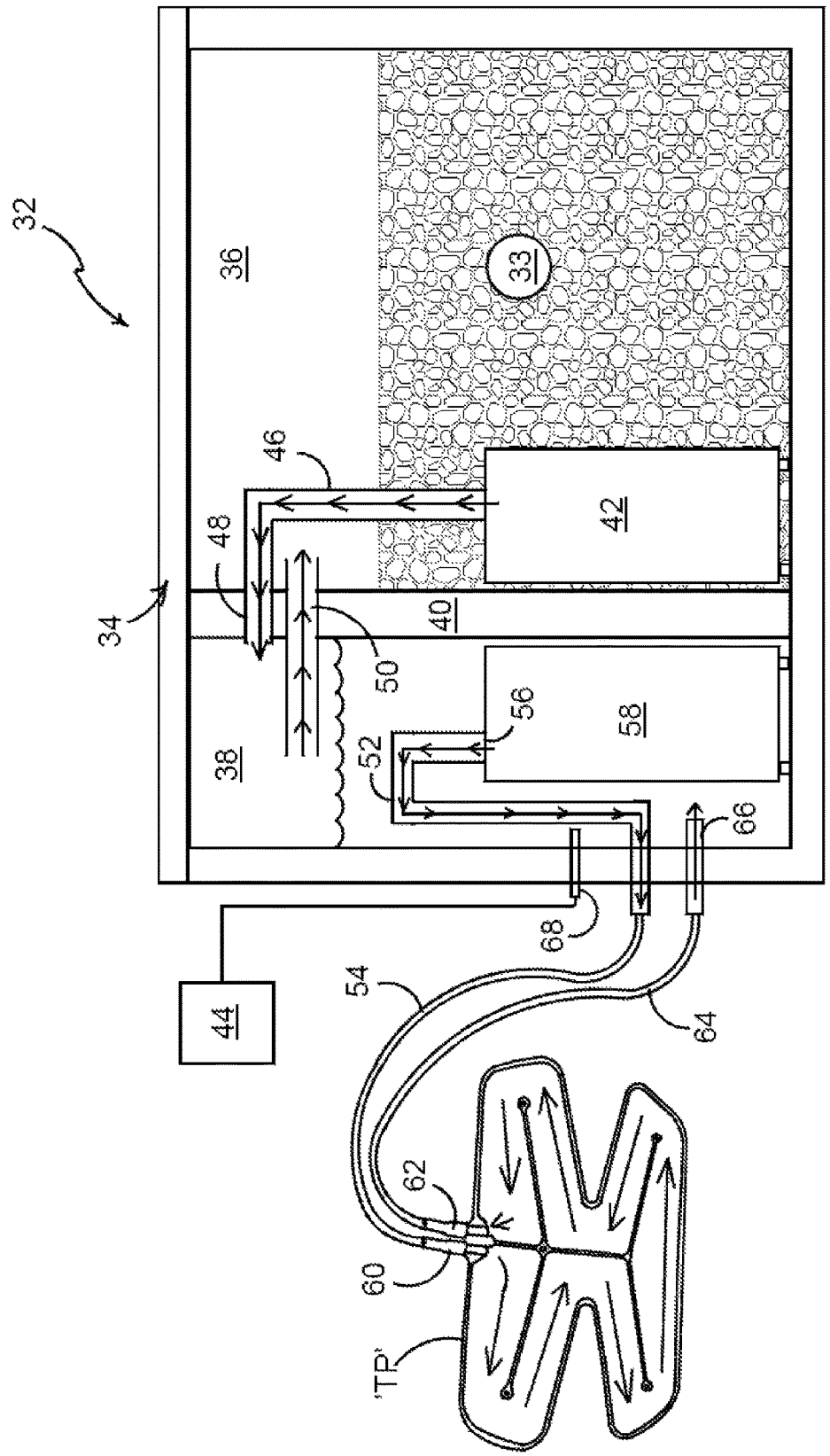
FIG. 5 is a schematic view of a fluid circulating system according to the invention, for use with a thermal pack.

Referring now to FIG. 5 of the drawings, in order to supply fluid to the thermal pack, a circulatory system 32 is provided. In this particular arrangement the fluid medium is chilled water, but it may be some other suitable fluid. The chilled water which would normally comprise an ice/water mixture 33 contained within a tank 34 which comprises two side by side compartments 36 and 38 respectively. The compartments are separated by a wall 40. Compartment 36 is larger than compartment 38 and has a capacity of approximately 6 liters in this embodiment, whereas the capacity of the tank 38 is approximately 2 liters.

Compartment 36 (the ice tank) is intended to contain iced water at a temperature of about, or at most, 4° C. whereas the tank 38 (the circulator tank) which receives fluid from the ice tank, is kept at a constant temperature of about 15° C.

The ice tank includes a submerged fluid exchange pump 42 which can be commanded by a suitable control system 44 to pump fluid through a supply conduit 46 and through a fluid passageway 48 in wall 40 to the circulator tank 38. A return overflow fluid passageway 50 is provided in the separator wall 40 below the supply fluid passageway 48. The arrangement is configured to maintain the water in the circulator tank at a level such that, when the system is operative, fluid is in constant flow from the circulator tank to the ice tank, through the overflow passageway 50.

A therapeutic thermal pack 'TP' receives chilled water from the circulator tank of the system through a feed supply line 52 and insulating hose 54 which is connected between an outlet 56 of a circulator pump 58 submerged within the circulator tank 38 and an inlet nozzle 60 of the thermal pack 'TP'. Fluid flows through the pack 'TP' in the direction of the arrows and is returned from outlet nozzle 62 of the thermal pack through an insulated return hose 64, which passes the circulated, and thus warmer water, through return conduit 66 into the lower part of the circulator tank 38.

A temperature probe 68 is positioned continuously to monitor the temperature of the fluid in the circulator tank 38 and is connected to the control system 44 which controls the operation of both the fluid exchange pump 42 and the circulator pump 58. Thus, when the temperature probe indicates that the temperature of the fluid return through return conduit 66 has risen or is rising above a predetermined level, the fluid exchange pump 42 is actuated so that cooler fluid from the ice tank 36 is supplied to the circulator tank 38 through the fluid passageway 48. Through the normal fluid convection cycle the warmer fluid in the circulator tank will rise and fluid therefore returns through the overflow fluid passageway 50 to be chilled in the ice tank 36. Accordingly there is normally, a continuous exchange of fluid between the ice tank 36 and the circulator tank 38.

Whereas the circulator pump preferably is in constant operation during the course of a predetermined therapy, the fluid exchange pump preferably operates intermittently as determined by the control system 44. The temperature probe 60 continuously monitors the temperature within the circulator tank and by appropriate instructions to the fluid exchange pump through the control system 44 there is a continuous exchange of fluid between the tanks 36, 38, respectively, in order to maintain the temperature of the fluid flowing through the thermal pack constant during the course of the therapeutic treatment.

However, the operation of the circulatory pump and/or the fluid exchange pump may be controlled by adjusting their respective flow rates in order to achieve a desired fluid exchange and thus substantially constant temperature of the fluid passing through the thermal pack.

Figure 6:
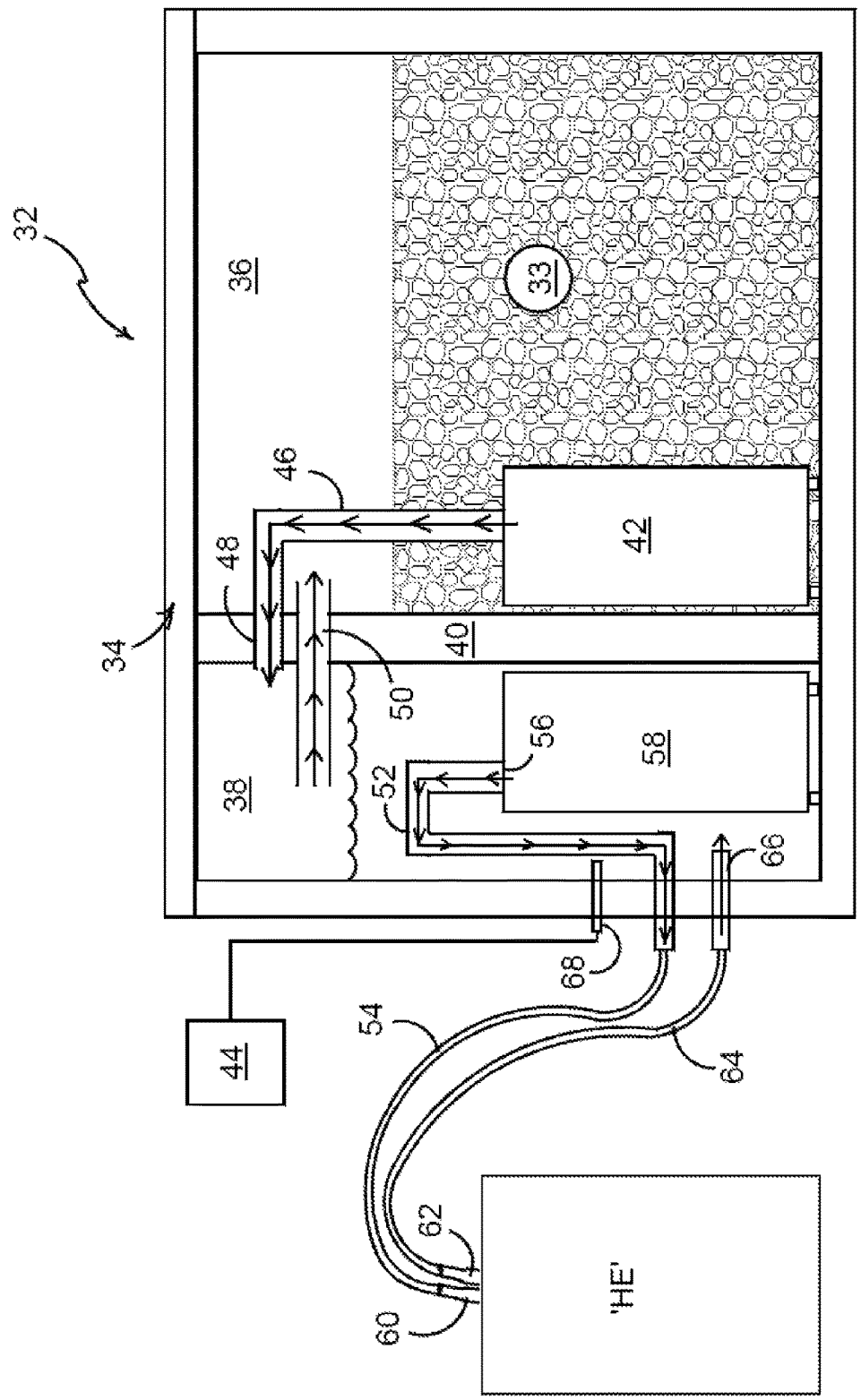
FIG. 6 is a schematic view of a fluid circulating system according to the invention for another use.

FIG. 6 of the drawings is similar to FIG. 1 except that fluid control system is connected to some other form of heat exchanger 'HE' rather than a therapeutic thermal pack. Like parts are designated like reference numerals.

The therapeutic treatment envisioned by the preferred embodiment of the present invention may also be administered together with intermittent compression therapy. The combined therapy helps to reduce initial swelling and continues to reduce swelling by forcing fluids into the lymphatic system, which in turn lowers the pressure on the limb and promotes fluid reabsorbtion. The therapy is also of help in the restoration of an oxygenated blood flow to increase healing.

It will be appreciated by those skilled in the art that several variations to the aforementioned embodiments are envisaged without departing from the scope of the invention. It will also be understood by those skilled in the art that any number of combinations of the aforementioned features and/or those shown in the appended drawings provide clear advantages over the prior art and are therefore within the scope of the invention described herein.

The invention claimed is:

1. A thermal pack for therapeutic treatment of a mammal, the pack comprising:
    a flexible, heat conductive liquid impermeable bladder having a fluid inlet and a fluid outlet, the bladder comprising a pair of superposed sheets secured together so as to provide a fluid passageway within the bladder; and
    a separator device within the fluid passageway and extending continuously throughout the fluid flow passageway, the separator device being secured by one or more studs to one or both of the superposed sheets and being otherwise unattached along its length to either one of the sheets;
    wherein the separator device comprises a multiplicity of discrete spaced-apart islands unattached to either one of the sheets and configured to provide a continuous and tortuous fluid flow path throughout the fluid passageway; the separator device comprising a structure or framework that prevents the fluid passageway from collapsing and maintains the superposed sheets in spaced apart relationship so as to maintain fluid flow through the pack when the pack is flexed, in use, out of the plane of the superposed sheets.

2. A thermal pack according to claim 1 wherein the separator device is formed from material which is less flexible relative to the superposed sheets.

3. A thermal pack according to claim 1 wherein the superposed sheets are formed from polyurethane and the separator device is formed from an injection molded plastics material.

4. A therapeutic treatment system comprising a thermal pack according to claim 1 and a fluid control system for supplying fluid to the thermal pack at a substantially constant temperature, wherein the fluid control system comprises a first volume of fluid separated from a second volume of fluid with a temperature differential therebetween and wherein an intermittently operable fluid exchange pump is provided together with a flow controller configured for mutual exchange of fluids between the first and second volumes of fluids in response to the temperature of fluid supplied by the fluid control system to the thermal pack in order to maintain flow of fluid therethrough at a substantially constant temperature.

5. A therapeutic treatment system according to claim 4, wherein the fluid control system comprises a first fluid containing tank comprising the first volume of fluid and a second fluid containing tank comprising the second volume of fluid, in which the fluid control system maintains a temperature differential between the first and second tanks, and wherein one of the tanks is adapted to supply fluid to the thermal pack so that the temperature of the fluid flowing therethrough is maintained at a substantially constant temperature, a circulatory pump being provided to create a fluid flow from the said one tank through the thermal pack, wherein the controller is operable to activate or control the operation of both the circulatory pump and the fluid exchange pump to provide a mutual exchange of fluid between the first and second fluid containing tanks in order to stabilize the temperature of the fluid supplied to the thermal pack.

6. A therapeutic treatment system according to claim 5, wherein the first fluid containing tank comprises the intermittently operable fluid exchange pump to supply fluid from that tank to the second fluid containing tank and wherein the second fluid containing tank comprises the circulator pump to supply fluid from the second tank to the thermal pack, a temperature sensor being provided to monitor the temperature of fluid flow through the thermal pack, and a return fluid passageway being provided to allow a mutual exchange of fluids between the first and second fluid containing tanks and wherein the controller causes said mutual exchange of fluids in response to information provided thereto by the temperature sensor.

7. A therapeutic treatment system according to claim 6, wherein one of the fluid pumps is submerged in the fluid of the fluid containing tank.

8. A therapeutic treatment system according to claim 7 wherein the first and second fluid containing tanks are provided in a single integrated unit with a separating wall between the tanks, wherein the intermittently operable fluid exchange pump from the first tank conveys fluid to the second tank through the separating wall and wherein the return fluid passageway is provided in the separating wall for the overflow return of fluid from the second tank to the first tank.

9. A therapeutic treatment system according to claim 4, wherein the fluid control system is provided in a single integral unit.

10. A therapeutic treatment system according to claim 4, wherein the fluid control system is configured to supply heated or chilled fluid to the thermal pack to maintain the pack at a substantially constant temperature for the duration of the therapeutic treatment.

11. A thermal pack according to claim 1, wherein the separator device is secured in position within the fluid passageway at a plurality of locations along its length by the one or more studs.

12. A thermal pack according to claim 11, wherein the one or more studs are external to the main outer perimeter of the pack.

13. A thermal pack according to claim 2, wherein the separator device comprises two components connected together by a bridging piece.

14. A thermal pack according to claim 13, wherein the separator device is secured in position within the fluid passageway by the one or more studs adjacent the inlet and outlet and on either side of the bridging piece.

15. A thermal pack for therapeutic treatment of a mammal, the pack comprising:
- a flexible, heat conductive liquid impermeable bladder having a fluid inlet and a fluid outlet, the bladder comprising a pair of superposed sheets secured together so as to provide a fluid passageway within the bladder; and
- a separator device within the fluid passageway and extending continuously throughout the fluid flow passageway, the separator device being secured by one or more studs to one or both of the superposed sheets and being otherwise unattached along its length to either one of the sheets;
- wherein the separator device is configured to provide a continuous and tortuous fluid flow path throughout the fluid passageway, the separator device comprising a structure or framework that prevents the fluid passageway from collapsing and maintains the superposed sheets in spaced apart relationship so as to maintain fluid flow through the pack when the pack is flexed, in use, out of the plane of the superposed sheets.

16. A thermal pack according to claim 15, wherein the separator device is secured in position within the fluid passageway at a plurality of locations along its length by the one or more studs external to the main outer perimeter of the pack.

17. A thermal pack according to claim 15, wherein the separator device is secured in position within the fluid passageway by the one or more studs adjacent the inlet and outlet.

18. A thermal pack according to claim 15, wherein the separator device comprises two components connected together by a bridging piece.

19. A thermal pack according to claim 18, wherein the separator device is secured in position within the fluid passageway by the one or more studs adjacent the inlet and outlet and on either side of the bridging piece.

* * * * *